US00PP08801P

United States Patent [19]

Ellis

[11] Patent Number: Plant 8,801

[45] Date of Patent: Jun. 28, 1994

[54] STRAWBERRY PLANT NAMED SERENATA

[75] Inventor: Jack R. Ellis, Buckinghamshire, England

[73] Assignee: Kenneth M. Muir, Essex, England

[21] Appl. No.: 64,696

[22] Filed: May 20, 1993

[51] Int. Cl.[5] ..... A01H 5/00

[52] U.S. Cl. ..... Plt./48

[58] Field of Search ..... Plt. 48, 49

*Primary Examiner*—James R. Feyrer

*Attorney, Agent, or Firm*—Foley & Lardner

[57] ABSTRACT

A new and distinct variety of strawberry plant named Serenata, characterized by its relatively dark pink colored flowers and dark green glossy leaves, together with its ability to set a reliable crop of small fruit.

2 Drawing Sheets

The present invention comprises a new and distinctive variety of strawberry plant referred to by the varietal name Serenata.

The new cultivar is a product of a planned breeding program. The basic objective of the breeding program was to create a new variety of strawberry having relatively dark pink flowers, while retaining other desirable characteristics such as the ability to set and bear a crop of fruit having acceptable size and flavor.

The new variety was originated from a cross made by the inventor in a controlled breeding program in Bourne End, Buckinghamshire, England. The female parent was a proprietary breeding line designated 82/12-10. The male parent was a breeding line designated 82/13-27, also referred to by the varietal name Pink Panda.

Serenata was discovered and selected by the inventor as a plant within the progeny of the stated cross in a controlled environment in Bourne End, Buckinghamshire, England. Asexual reproduction of the new variety, as performed by or under the supervision of the inventor both at Bourne End and Weeley Heath, England, has demonstrated that the combination of characteristics as herein disclosed for the new cultivar are firmly fixed and are retained through successive generations of asexual reproduction.

Serenata has not been observed under all possible environmental conditions. The phenotype may vary somewhat with variations in environment, without, however, any variation in genotype. The following observations, measurements and values describe the new cultivar as grown in Bourne End and Weeley Heath, England under conditions which closely approximate those generally used in commercial practice.

The following traits have been repeatedly observed and are determined to be basic characteristics of Serenata, which in combination, distinguish this strawberry plant as a new and distinct variety:

1. An abundance of relatively dark pink flowers.
2. Serenata blooms in southern England continuously from late April until frost which typically occurs in November or December.
3. Relatively small, dark green glossy leaves.
4. Prominent stamens and gynoecium produce a relatively expansive deep yellow center which provides a pleasant contrast with the deep pink flowers and dark green leaves.
5. Serenata produces runners prolifically, with the runners readily rooting.

6. Serenata produces an abundance of relatively small, elliptically shaped fruit which per se is not distinctive.
7. The new cultivar has been discovered to have a chromosome count of 58, two more than the typical cultivated strawberry plant.

The new variety is most similar to the male parent Pink Panda, which also has pink colored flowers. However, the flowers of Serenata are a much darker pink. In addition, Serenata has dark green glossy leaves and is a good fruit producer. By comparison, Pink Panda bears little fruit.

The accompanying color photographic drawings comprise sheet 1, which shows a typical specimen plant of the new variety, and sheet 2, which illustrates in greater detail typical flowers, leaves and fruit of the new cultivar. The colors appearing in the photographs are as true as possible with color illustrations of this type.

In the following description, color references are made to The Royal Horticultural Society Colour Chart (R.H.S.), except where general colors of ordinary significance are referred to.

Parentage:

*Male parent.*—No. 82/13-27, Pink Panda.

*Female parent.*—No. 82/12-10.

Propagation: Runner production is prolific and the runners are quick rooting. Offsets are vigorous.

Plants:

A. *Overall size.*—Approximately 10–11 cm in height when fully grown, excluding roots measured from top of soil surface to top of leaves. Plant is approximately 18–24 cm in diameter at center, but with runners the entire width of the plant can be as much as 120–130 cm, with new plants appearing on the runners radially spaced apart about 18–22 cm. The runners resemble spokes of a wheel.

B. *Preferred planting.*—In southern England, October or March, in locations having full sun. Peak production occurs in September.

C. *Leaves.*—1. Arrangement: Each leaf is composed of three separate leaflets which overlap slightly. 2. Size: Each leaflet of large, fully mature leaves can be as large as approximately 8 cm long and 7 cm wide; entire leaf comprised of three leaflets is approximately 10 cm long and 15 cm wide. 2. Shape: Generally round, transversely concave when first expanding, becoming generally flat; base is acute to round and tip is generally rounded. 3. Color: Upper surface, dark glossy green, approximately 139A; under surface approximately 148A. 4. Growth habit: Low and open. 5. Margin: Mildly serrated. 6. Petiole: Petiole is approximately 7–8 cm in length, 139D in color, and has a hirsute surface; stipules are 1–2 cm in length and brown in color;

D. *Disease resistance.*—Resistance to powdery mildew is typical for cultivars of this species; no other disease problems have been noted to date.

Inflorescence:

A. *Size and shape.*—Six petals, each generally round; concave or cup shaped when opening; when fully open, overall flower diameter is approximately 2.5 cm.

B. *Peduncles.*—Relatively long; green with anthocyanin pigmentation.

C. *Pedicels.*—Single, relatively long and non-rigid; generally green with anthocyanin pigmentation in mature pedicels; slight pubescence.

D. *Abundance.*—Very floriferous.

E. *Color.*—Relatively dark pink; when just opening, approximately 61A, fading non-uniformly to approximately 61B or even lighter; underside approximately 65A.

F. *Stamens.*—Stamens are abundant in number and provide a substantial deep yellow flower center, approximately 12C; good production of pollen.

G. *Pistils.*—Typical for species, deep yellow.

H. *Calyx.*—Small calyx, deep pink in color; individual sepals are shield shaped.

Fruit:

A. *Overall size and shape.*—Fruit is relatively small in size and generally elliptical in shape, being approximately 1.8 cm wide and 3 cm long.

B. *Seeds.*—Level with surface of fruit.

C. *Juiciness.*—Slightly dry.

D. *Taste.*—Generally sweet, with musk flavor.

E. *Color.*—The exterior color is a generally light red, closest to 42A; flesh ranges from near white in center to pinkish red toward exterior.

F. *Exterior surface.*—Fruit is relatively firm; glossy surface.

G. *Characteristics of flesh and core.*—Flesh is relatively soft; core is solid relatively small.

H. *Aroma.*—Floral aroma.

I. *Keeping qualities.*—Ripe fruit stays fresh on plant approximately 3–4 days depending on temperature; after picking, keeping quality is average.

Disease resistance: Good.

General Observations: Serenata is distinctive primarily due to its relatively dark pink colored flowers and dark green glossy leaves, together with its ability to flower and set a reliable crop of small fruit formerly spring to frost. The characteristics of the fruit are not distinguishing and Serenata is a unique new cultivar primarily due to its ornamental value.

I claim:

1. A new and distinct variety of strawberry plant named Serenata, as illustrated and described.

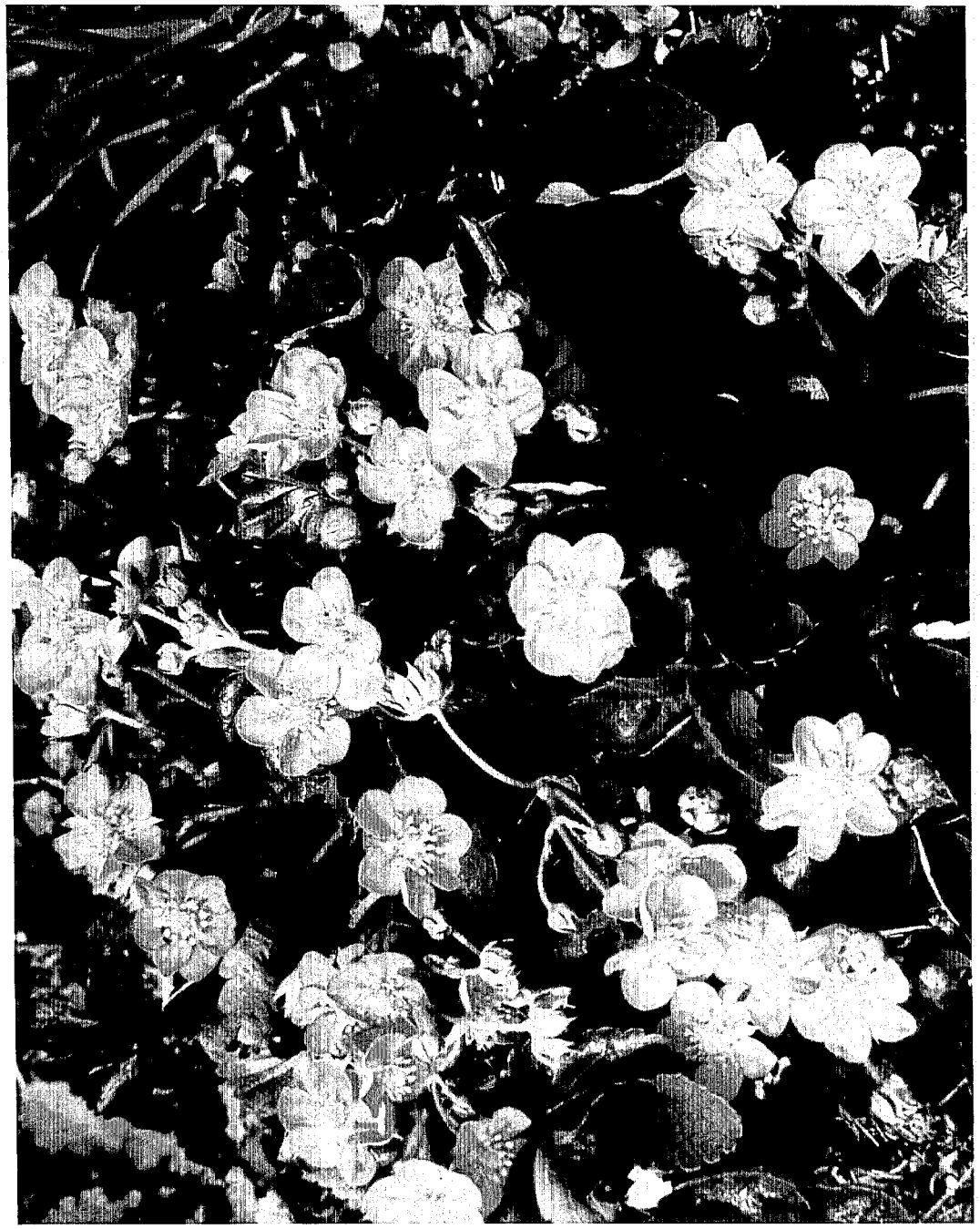

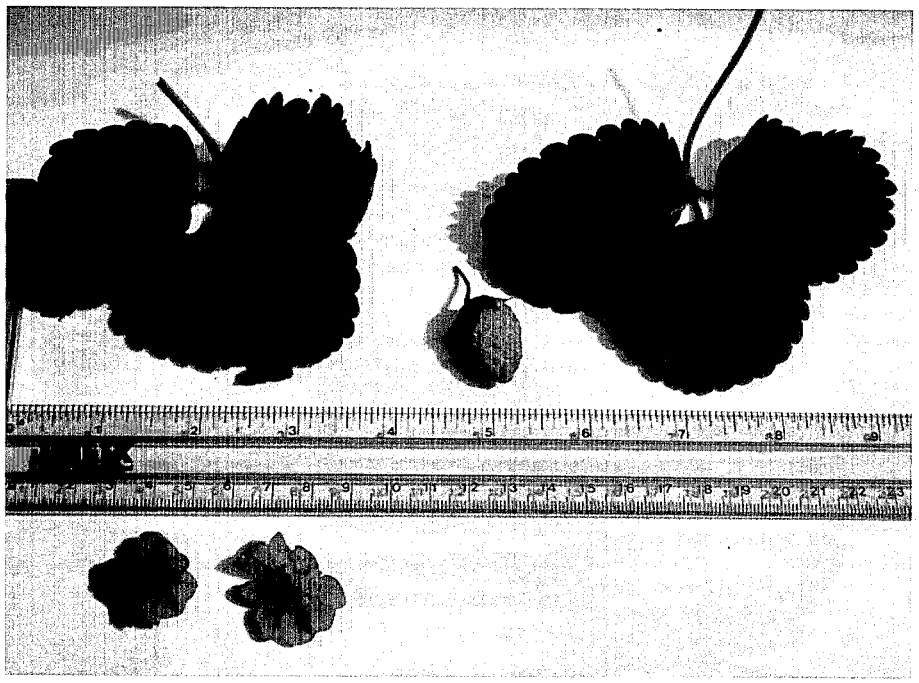

* * * * *